US00PP08195P

United States Patent [19]

Zaiger et al.

[11] Patent Number: Plant 8,195

[45] Date of Patent: Apr. 6, 1993

[54] PEACH TREE "SNOWBRITE"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95351

[21] Appl. No.: 811,721

[22] Filed: Dec. 23, 1991

[51] Int. Cl.[5] ..... A01H 5/00

[52] U.S. Cl. ..... Plt./42.1

[58] Field of Search ..... Plt./42.1

[56] References Cited

U.S. PATENT DOCUMENTS

P.P. 5,821 12/1986 Zaiger et al. ..... Plt. 42.1

*Primary Examiner*—James R. Feyrer

[57] ABSTRACT

A new and distinct variety of peach tree which has the following unique combination of desirable features that are outstanding in a new variety.

1. The ability of the fruit to stay firm on the tree 6 to 7 days after maturity (picking ripe).
2. Fruit with excellent flavor and eating quality.
3. Bearing very firm white flesh fruit with good shipping and storage quality.
4. Heavy and regular bearing of large size fruit.
5. Fruit with early maturity. 6. Fruit with a high degree of attractive red skin color, coloring 6 to 7 days before maturity.

1 Drawing Sheet

ORIGIN OF THE VARIETY

The herein new variety of peach tree was originated by us in our experimental orchard located near Modesto, Calif. as a second generation seedling from a cross between two selections. The female parent was a selection from a cross beween O'Henry Peach (U.S. Plant Pat. No. 2,964) and Giant Babcock Peach (U.S. Plant Pat. No. 1,353) and the male parent originated from a cross of May Grand Nectarine (U.S. Plant Pat. No. 2,794) and Sam Houston Peach (Non-patented). We grew and maintained a large number of these second generation seedlings under close observation, one such seedling which is the present variety, having especially desirable fruit characteristics was selected for reproduction and commercialization.

ASEXUAL REPRODUCTION OF THE VARIETY

The present new and distinct variety of peach tree was asexually reproduced by budding, as performed by us, in our experimental orchard located near Modesto, Calif. and shows that all characteristics come true to form and are established and transmitted through succeeding propagations.

SUMMARY OF THE VARIETY

The present variety of peach tree is of large size, vigorous, upright in growth and a regular and productive bearer of large, very firm, white flesh, freestone fruit with excellent flavor and eating quality. The fruit is further characterized by coloring 6 to 7 days before maturity, having an attractive red skin color and the ability to ship to long distance markets. The present variety of peach tree is further characterized in comparison to Giant Babcock Peach (U.S. Plant Pat. No. 1,353) by maturing fruit approximately 34 days earlier, having firmer white flesh with greater shipping and storage ability and a higher degree of attractive red skin color.

BRIEF DESCRIPTION OF THE PHOTOGRAPHS

The accompanying photographs show reproductions in color of typical specimens of foliage and fruit of the new variety of peach tree, with the upper and lower surface the foliage being illustrated, an exterior and a sectional view of the fruit being shown with a stone remaining in place. The photographs were taken shortly after being picked at maturity (firm ripe) and the colors are as nearly true as is reasonably possible in a color representation of this type.

DESCRIPTION OF THE VARIETY

The following is a botanical description of the peach tree, its flowers, foliage and fruit as based on observations of the specimens grown in our experimental orchard near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Bearer.*—Regular.
- *Productivity.*—Productive.

Trunk:
- *Size.*—Medium to stocky.
- *Texture.*—Medium shaggy.
- *Color.*—Grayish brown to brown (5-E-3) to (5-E-5).

Branches:
- *Size.*—Medium.
- *Texture.*—Smooth to medium rough.
- *Lenticels.*—Medium size. Medium number.
- *Color.*—Oak-brown to brown (5-E-6) to (5-E-8).

Leaves:
- *Size.*—Large. Average length — 6½". Average width — 1⅝".
- *Form.*—Lanceolate. Acutely pointed.
- *Thickness.*—Medium.
- *Margin.*—Crenate.
- *Petiole.*—Medium length. Medium thickness.

*Glands.*—Reniform. Number varies from 1 to 4. Average number 2. Large size. Positioned on base of leaf blade and upper portion of petiole.

*Color.*—Upper surface green to dark green (27-F-4) to (27-F-6). Lower surface light green to jade green (27-E-3) to (27-E-5).

Flower buds:

*Size.*—Large.

*Form.*—Plump.

*Pubescence.*—Pubescent.

Flowers:

*Size.*—Large — showy.

*Blooming period.*—First Bloom — Mar. 1, 1989. Full Bloom — Mar. 8, 1989. Varies slightly due to weather variations.

*Pollen.*—Present.

*Color.*—Pink.

Fruit:

*Maturity when described.*—Firm ripe.

*Date of first picking.*—Jun. 10, 1989.

*Date of last picking.*—Jun. 17, 1989.

*Size.*—Large. Average axial diameter — $2\frac{3}{4}''$. Average transversely in suture plane — $2\frac{3}{4}''$.

*Form.*—Globose — nearly symmetrical slightly retuse at stem end.

*Suture.*—Shallow — extends from base to apex.

*Ventral surface.*—Usually rounded — some fruit very slightly lipped.

*Apex.*—Varies from rounded to sligth piston point.

*Base.*—Slightly retuse.

*Cavity.*—rounded to slightly elongated in suture plane. Average depth — $\frac{1}{2}''$. Average breadth — $\frac{7}{8}''$.

Skin:

*Thickness.*—Medium.

*Texture.*—Medium. Tenacious to the flesh.

*Down.*—Moderate. Medium length.

*Tendency to crack.*—None.

*Color.*—Yellowish white (3-A-3) to light yellow (3-A-5) ground color. Overspread wih madder red (9-A-7) to lake red (9-C-8).

Flesh:

*Ripens.*—Evenly.

*Texture.*—Very firm.

*Fibers.*—Few — small — tender.

*Amygdalin.*—Undeteched.

*Eating quality.*—Excellent.

*Flavor.*—Excellent, subacid — mild.

*Juice.*—Moderate.

*Aroma.*—Moderate.

*Color.*—White to oyster white (2-A-1) to (2-A-2). Pit cavity — grayish yellow to yellowish gray (3-B-3) to (3-B-5).

Stone:

*Type.*—Freestone — flesh adheres to stone in small areas on some fruit.

*Size.*—Large. Average length — $1\frac{3}{8}''$. Average width — 15/16". Average thickness — 9/16".

*Form.*—Obovoid.

*Apex.*—Acuminate.

*Base.*—Straight to slightly oblique.

*Sides.*—Equal to unequal, usually unequal.

*Surface.*—Furrowed toward apex, pitted toward base.

*Ridges.*—Rounded.

*Tendency to split.*—Very slight.

*Color.*—Light brown to brown (6-C-4) to (6-D-4).

Use: Dessert.

*Market.*—local and long distance.

Keeping quality: Good.

Storage quality: Good.

The present variety of peach tree, its flowers, foliage and fruit herein described may vary in slight detail due to climatic, soil type and cultural practices under which the variety may be grown; the present description being of the variety grown by us under the ecological conditions prevailing near Modesto, Calif.

We claim:

1. A new and distinct variety of peach tree substantially as illustrated and described, which is of large size, vigorous, upright in growth and a regular and productive bearer of large, very firm, white flesh, freestone fruit with excellent flavor and eating quality; the fruit is further characterized by coloring 6 to 7 days before maturity and in comparison to Giant Babcock Peach (U.S. Plant Pat. No. 1,353) has firmer white flesh, a higher degree of attractive red skin color and matures approximately 34 days earlier.

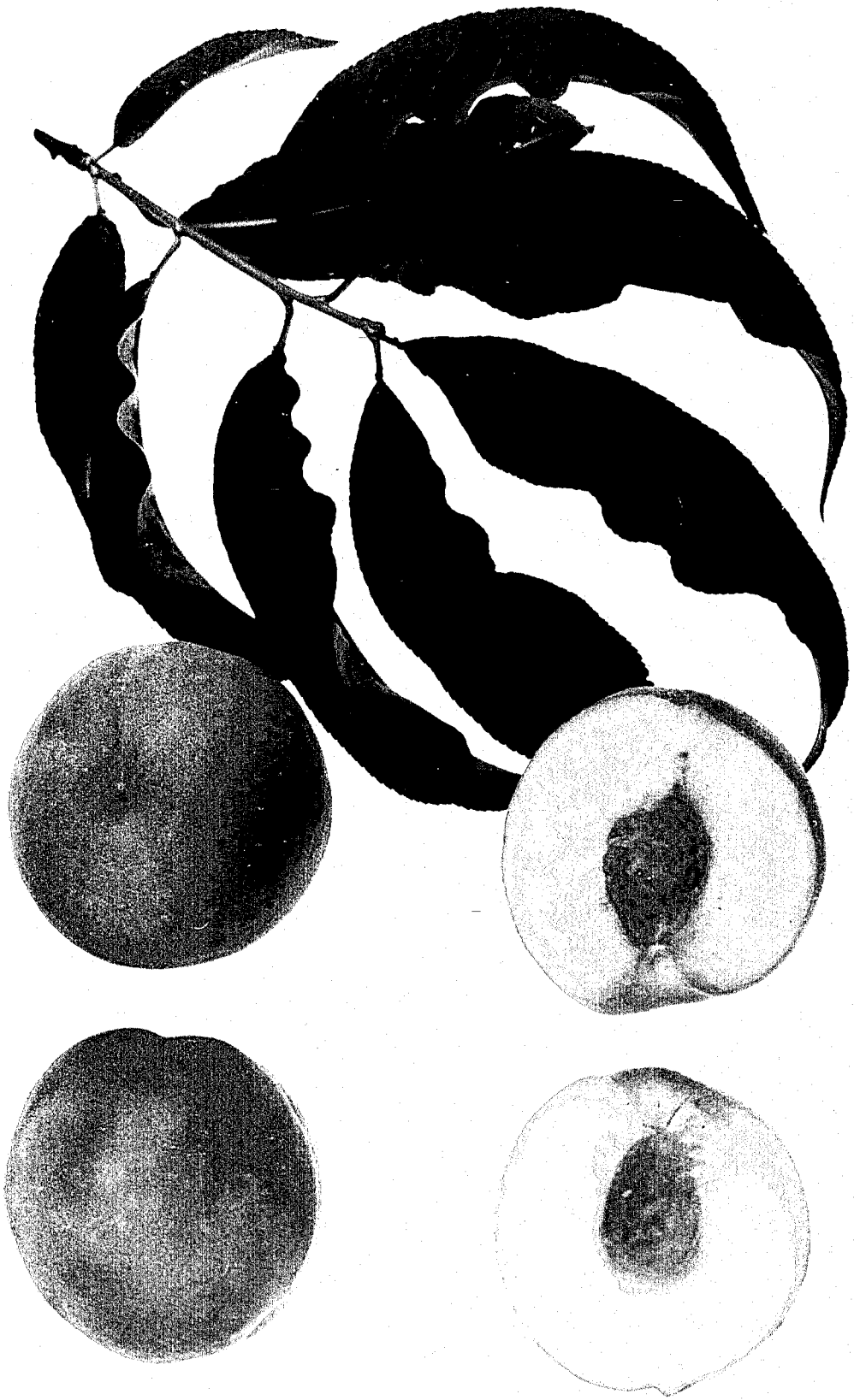

* * * * *